United States Patent [19]

Hirschberg et al.

[11] Patent Number: 4,922,926
[45] Date of Patent: May 8, 1990

[54] ARRANGEMENT FOR DELIVERING MEDICATIONS IN AN IMPLANTABLE MEDICAL DEVICE

[75] Inventors: Jakub Hirschberg, Taeby; Lars Botvidsson, Solna; Ulf Fahlstroem, Stockholm, all of Sweden

[73] Assignee: Siemens Aktiengesellschaft, Berlin and Munich, Fed. Rep. of Germany

[21] Appl. No.: 255,545

[22] Filed: Oct. 11, 1988

[30] Foreign Application Priority Data

Oct. 16, 1987 [DE] Fed. Rep. of Germany ....... 3735137

[51] Int. Cl.$^5$ ............................................. A61N 1/00
[52] U.S. Cl. .................................. 128/785; 128/786; 128/419 P; 604/93
[58] Field of Search ............ 128/784, 785, 786, 419 P; 604/93, 175, 9, 185, 20, 21

[56] References Cited

U.S. PATENT DOCUMENTS

| | | | |
|---|---|---|---|
| 4,506,680 | 3/1985 | Stokes | 128/786 |
| 4,577,642 | 3/1986 | Stokes | 128/784 |
| 4,711,251 | 12/1987 | Stokes | 128/784 |
| 4,784,161 | 11/1988 | Skalsky et al. | 128/785 |
| 4,819,662 | 4/1989 | Heil, Jr. et al. | 128/786 |

FOREIGN PATENT DOCUMENTS

| | | |
|---|---|---|
| 0047013 | 3/1982 | European Pat. Off. . |
| 0149693 | 7/1985 | European Pat. Off. . |
| 2502884 | 7/1976 | Fed. Rep. of Germany . |
| WO86/02824 | 5/1986 | PCT Int'l Appl. . |

Primary Examiner—Lee S. Cohen
Assistant Examiner—Scott Getzow
Attorney, Agent, or Firm—Hill, Van Santen, Steadman & Simpson

[57] ABSTRACT

An arrangement for delivering medications in an implantable medical device, such as a heart pacemaker, has at least two containers or receptacles for the medication disposed below the surface of a portion of the implanted device, each container terminating in an opening having the size of a pore in the surface of the implanted device to permit the medication to be delivered from the container to surrounding tissue. The structure permits the medication to be delivered at specific regions of tissue, and in a manner which permits control of the medication dose.

11 Claims, 1 Drawing Sheet

ARRANGEMENT FOR DELIVERING MEDICATIONS IN AN IMPLANTABLE MEDICAL DEVICE

BACKGROUND OF THE INVENTION

1. Field of the Invention

The present invention is directed to an arrangement for delivering medication in an implantable medical device.

2. Description of the Prior Art

A heart pacemaker electrode is described in U.S. Pat. No. 4,577,642 having components therein for delivering medication to tissue surrounding the electrode. At its distal end, the electrode has an electrode head with an internal cavity therein filled with medication. The cavity has an open end covered by an electrode tip consisting of sintered material, through which the medication can migrate to the surface of the electrode tip for delivery to tissue in contact therewith. The medication is intended to prevent the formation of both thromboses and inflammations in the region of the electrode head. In the heart pacemaker electrode of this type, the medication is not distributed over the surface in a controllable fashion, and only one type of medication can be delivered at a time.

SUMMARY OF THE INVENTION

It is an object of the present invention to provide an arrangement for delivering medications in an implantable medical device which permits the medication to be delivered in a controllable fashion in defined tissue regions.

It is a further object of the present invention to provide such an arrangement which permits more than one medication to be delivered at a time.

The above object is achieved in accordance with the principles of the present invention in an implantable medical device having at least two containers for storing medication, each of the containers being in communication with at least one opening in a surface of the device having the size of a pore. An arbitrary number of containers or receptacles, which can contain respectively different medications, can be arranged at defined surface regions of the device. In one embodiment, the containers form slight depressions in the surface region of the device at which the containers are disposed, which permit tissue ingrowth.

The structure disclosed herein is particularly suitable for use in heart pacemaker systems. The arrangement may be disposed at one or more selected surface regions of the heart pacemaker system. The arrangement may be disposed, for example, in a heart pacemaker electrode, wherein the containers can be arranged both in the electrode head and at tissue-fastening structures such as collars or bristles attached in the region of the electrode head. The containers can be filled with different medications such as, for example, cortisone and/or penicillin. Other portions of the heart pacemaker system such as the electrode ring (if a bipolar electrode is used) a fastening clamp for anchoring the electrode at a vein, and the connector portion of the heart pacemaker housing may also be provided with containers filled with medication.

In a further embodiment of the invention, the containers have respective longitudinal axes which reside at respectively different angles with the surface region of the implanted device. The angle at which tissue ingrowth occurs in each container can thus be defined.

In a further embodiment of the invention, the containers are conical, tapering to a smallest portion in communication with the surrounding tissue via the pore-sized hole in the surface of the implanted device. This form of container can be manufactured in a relatively simple manner by a laser beam.

In another embodiment of the invention, the containers consist of at least two intersecting blind holes. A relatively large container having at least two openings, each having the size of a pore in the surface of the implanted device, is thereby achieved. Tissue growing into the containers can meet at the intersecting interior of the container through these openings. A reliable anchoring of the portion of the implanted device at which such intersecting containers are disposed is thereby established.

DESCRIPTION OF THE PREFERRED EMBODIMENTS

Figure 1:
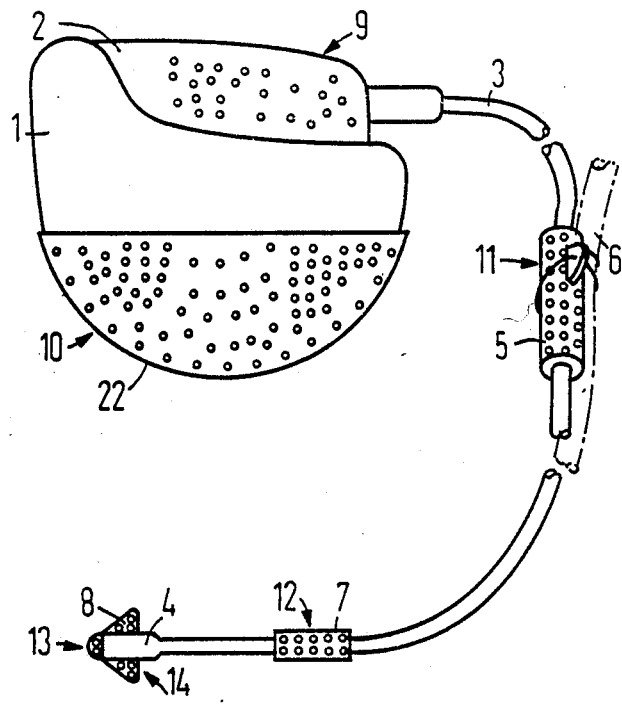
FIG. 1 is a side view of a heart pacemaker system employing a medication delivery arrangement constructed in accordance with the principles of the present invention.

As shown in FIG. 1, an implanted medical device such as a heart pacemaker system includes a pacemaker housing 1 having a connector 2 for an electrode 3 which has a distal end provided with an electrode head 4 and tissue-fastening structure 8. The electrode 3 may be anchored at a vein 6 of a patient with a fastening clamp 5, and may be provided with a ring electrode 7 to form a bipolar electrode. The different components of the heart pacemaker system are respectively provided with medication delivery structure 9, 10, 11, 12, 13 and 14. The pacemaker housing 1 may be provided with a plastic coating or covering 22 in which the medication delivery structure 10 is disposed. The connector 9 may also include such medication delivery structure 9. The medication delivery structures 9 and 10 can delivery medications which prevent inflammation which may arise around the implanted pacemaker.

The fastening clamp 5 may also deliver anti-inflammation medication with a medication delivery structure 11. The ring electrode 7 may be provided with a medication delivery structure 12 for delivering a mediation against thrombosis which may otherwise form in the region of the ring electrode 7.

Figure 2:
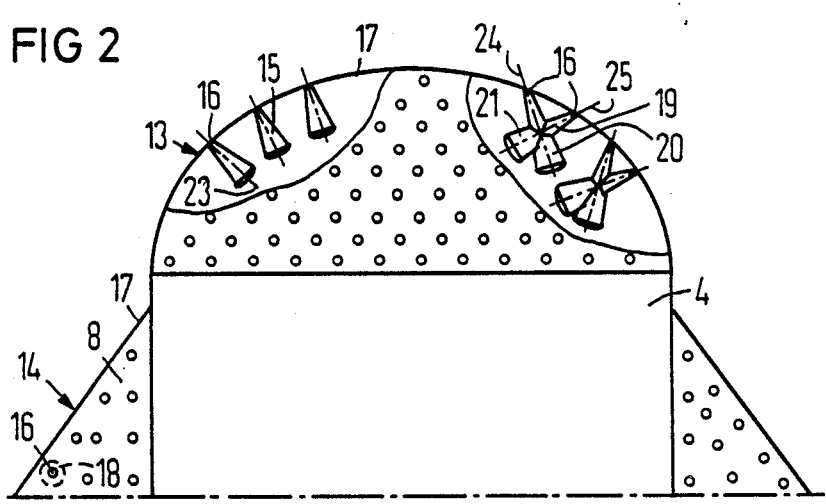
FIG. 2 is an enlarged side view, partly in section, of an electrode head embodying a medication delivery arrangement constructed in accordance with the principles of the present invention.

FIG. 2 shows the electrode head 4 with tissue-fastening structure 8 thereon, provided with respective medication delivery structure 13 and 14. The structure 13 and 14 consists of conically fashioned containers or receptacles 15 and 18, each of which is in communication with an opening 16 having the size of a pore in the surface region 17 of the electrode head 4, or the surface region of the fastening structure 8. The containers 15 and 18 can be disposed arbitrarily close to each other, and in different regions may contain different medications. Thus, for example, the container 15 may hold medication for preventing thromboses from arising, and the container 18 may be filled with a medication for preventing inflammation.

FIG. 2 also shows a further embodiment wherein containers 19 are provided consisting of two intersecting blind holes 20 and 21. Such containers 19 are relatively large and thus hold more medication. The medication emerging from the openings spread in the tissue region of the heart pacemaker system at which the respective structure 9 through 14 is disposed.

Each of the containers 15, 18 and 19 form slight depressions in the relevant region which permit tissue ingrowth, so as to anchor certain portions of the implanted device. For this purpose, the respective longitudinal axes 23, 24 and 25 of the containers 15, 18 and 19 are disposed at respectively different angles with respect to the surface of the implanted device, so that the angle at which tissue ingrowth occurs can be prescribed. The containers 19 formed by the intersecting blind holes have an advantageous shape for anchoring a portion of the implanted device, because the tissue meets in the interior of such a container 19, coming from the respective openings, and con grow together.

Although the arrangement has been described above in connection with a heart pacemaker system, the structure disclosed herein can be used in any type of implantable medical device wherein delivery of medication is desired.

Although modifications and changes may be suggested by those skilled in the art it is the intention of the inventors to embody within the patent warranted hereon all changes and modifications as reasonably and properly come within the scope of their contribution to the art.

We claim as our invention:

1. An arrangement for delivering medication in an implantable medical device, said device having a plurality of surface regions, said arrangement comprising:
    at least two containers, said containers including means for storing medication disposed in said implantable medical device at at least one of said surface regions, each of said containers being in communication with said at least one surface region via an opening in said surface region having the size of a pore adapted to dispense medication from the container to tissue surrounding said surface region.

2. An arrangement as claimed in claim 1, wherein each of said containers has a longitudinal axis, and wherein said longitudinal axes of said containers are disposed at respectively different angles with respect to said at least one surface region.

3. An arrangement as claimed in claim 1, wherein said containers are conical.

4. An arrangement as claimed in claim 1, wherein each of said containers consists of at least two intersecting blind holes.

5. A heart pacemaker system comprising:
    a housing;
    an electrode lead;
    means for connecting said electrode lead to said housing;
    means disposed in said housing and electrically connected to said electrode lead via said means for connecting for electrically stimulating body tissue;
    a stimulation delivering tip disposed at a distal end of said electrode lead remote from said housing;
    each of said housing, said means for connecting and said tip having a surface; and
    means disposed in at least one of said housing, said means for connecting, and said tip, for delivering medication to surrounding tissue comprising at least two containers adapted for storing medication, each of said containers having a pore-sized opening in communication with the respective surface of said housing, said means for connecting or said tip adapted for delivering medication from the container to said tissue.

6. A heart pacemaker system as claimed in claim 5, further comprising means disposed at said distal end of said electrode lead for fastening said distal end of said electrode lead to said surrounding tissue, said means for fastening having a surface, and means for delivering medication disposed in said means for fastening.

7. A heart pacemaker system as claimed in claim 5, further comprising a ring electrode on said electrode lead spaced from said distal end and forming a bipolar electrode with said tip, said ring electrode having a surface and having means for delivering medication disposed therein.

8. A heart pacemaker system as claimed in claim 5, further comprising means for clamping said electrode lead to a vein, said means for clamping having a surface and further comprising means for delivering medication in said means for clamping.

9. A heart pacemaker system as claimed in claim 5, wherein each of said containers has a longitudinal axis, and wherein said longitudinal axes of said containers are disposed at respectively different angles with respect to the surface with which said containers communicate.

10. A heart pacemaker system as claimed in claim 5, wherein said containers are conical.

11. A heart pacemaker system as claimed in claim 5, wherein said containers consist of two intersecting blind holes.

* * * * *